DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JUNE 5, 1973

911 O.G. 8

T911,007
AROMATIC POLYMERS

Ian Charles Taylor, Bengeo, England, assignor to Imperial Chemical Industries Limited, London, England

Filed June 27, 1972, Ser. No. 266,728
Claims priority, application Great Britain, July 5, 1971, 31,414/71
Int. Cl. C07c *147/06*
U.S. Cl. 260—607 A
No Drawing. 7 Pages Specification

Polyarylene sulphides are homogeneously oxidized to polyarylene sulphones according to the process disclosed, which is characterized by first dissolving the oxidant that is selected in a sulfuric acid medium, then adding the polyarylene sulphide to the oxidant-containing sulfuric acid medium. The oxidation reaction is conducted in solution and may be terminated, if desired, at any stage of reaction to produce a polymer which is homogeneously oxidized throughout to an intermediate oxidation stage between the polyarylene sulphide and the ultimate polyarylene sulphone. Partially oxidized polymers are conveniently fabricated into fibers without need of initial filtration.

Illustrative is the oxidation of poly(phenylene sulphide sulphone) where a 30 weight percent solution of hydrogen peroxide in water is added to concentrated sulfuric acid and the resulting solution is added to the poly(phenylene sulphide sulphone) at a temperature between about —30° and 100° C. The resulting polymer had repeating units of the formula:

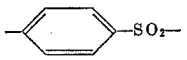

Only partially oxidized polymers are prepared by using sufficient oxidant, such as hydrogen peroxide, to oxidize only a portion of the thioether linkages to sulphone linkages. Partially oxidized polymers thus formed where the number of —$SO_2$— and —$SO_2$— linkages are about equal are soluble in concentrated sulfuric acid and may be wet spun into silky fibers.